(12) United States Patent
Eble

(10) Patent No.: US 9,427,713 B2
(45) Date of Patent: Aug. 30, 2016

(54) MIXING, STIRRING OR DISPERSING APPARATUS AND METHOD USING A CONTAINER WITH A DIAPHRAGM WALL PART WITH A DRIVE SWITCHED OFF CONDITION BASED ON A DIAPHRAGM LOADING CAPACITY

(75) Inventor: Erhard Eble, Bad Krozingen (DE)

(73) Assignee: IKA—Werke GmbH & Co. KG, Staufen (DE)

( * ) Notice: Subject to any disclaimer, the term of this patent is extended or adjusted under 35 U.S.C. 154(b) by 689 days.

(21) Appl. No.: 13/877,099

(22) PCT Filed: Aug. 4, 2011

(86) PCT No.: PCT/EP2011/003921
§ 371 (c)(1),
(2), (4) Date: Mar. 29, 2013

(87) PCT Pub. No.: WO2012/041415
PCT Pub. Date: Apr. 5, 2012

(65) Prior Publication Data
US 2013/0194889 A1    Aug. 1, 2013

(30) Foreign Application Priority Data
Oct. 1, 2010   (DE) .......................... 10 2010 047 305

(51) Int. Cl.
*B01F 11/04* (2006.01)
*B01F 13/04* (2006.01)
(Continued)

(52) U.S. Cl.
CPC .............. *B01F 7/1695* (2013.01); *B01F 11/04* (2013.01); *B01F 13/04* (2013.01); *B01F 13/047* (2013.01); *B01F 15/00922* (2013.01); *G01N 2035/00534* (2013.01)

(58) Field of Classification Search
CPC .... B01F 7/1695; B01F 11/04; B01F 13/047; B01F 13/04; B01F 15/00922; G01N 2035/00534
See application file for complete search history.

(56) References Cited

U.S. PATENT DOCUMENTS 2,692,125 A * 10/1954 Alvin Light Curtis ................... B01F 7/1655 366/251
3,913,895 A * 10/1975 de Bruyne .............. B01F 11/04 366/247
(Continued)

FOREIGN PATENT DOCUMENTS

DE        102006030056 B3    6/2007
EP              0409039 A1 *  1/1991  .............. B01F 11/04
(Continued)

*Primary Examiner* — Charles Cooley
(74) *Attorney, Agent, or Firm* — Volpe and Koenig, P.C.

(57) ABSTRACT

Mixing, stirring or dispersing method using a corresponding apparatus (1) with a housing (2) and a container (3). The container (3) has a mixing chamber (4), into which mixing chamber (4) a rod-like element (6) projects. At the entrance into the mixing chamber (4), this rod-like element (6) is connected to a membrane (8), which membrane (8) is part of a wall (9) of the container (3). In order to process the contents of the mixing chamber (4), the rod-like element (6) is made to move, together with the membrane (8), by a drive (7). In order to avoid unintentional failure of the membrane (8), within the context of the method, the number of revolutions of the drive (7) is counted and the drive is switched off upon reaching a maximum number of revolutions permitted for the loading capability of the membrane (8) and the resulting number of load variations.

24 Claims, 3 Drawing Sheets

(51) Int. Cl.
  *B01F 7/16* (2006.01)
  *B01F 15/00* (2006.01)
  *G01N 35/00* (2006.01)

(56) References Cited

U.S. PATENT DOCUMENTS

| | | | |
|---|---|---|---|
| 3,955,802 A * | 5/1976 | de Bruyne | B01F 11/04 366/243 |
| 3,998,435 A * | 12/1976 | de Bruyne | B01F 11/04 366/243 |
| 7,648,095 B2 | 1/2010 | Jagle | |
| 8,317,389 B2 * | 11/2012 | Jagle | B01F 11/04 366/208 |
| 2004/0111237 A1 | 6/2004 | Vlok | |
| 2006/0245298 A1 * | 11/2006 | Jagle | B01F 7/1695 366/244 |
| 2007/0182359 A1 | 8/2007 | Wahler | |
| 2010/0034048 A1 * | 2/2010 | Jagle | B01F 11/04 366/118 |
| 2011/0046996 A1 | 2/2011 | Foucher et al. | |
| 2013/0194889 A1 * | 8/2013 | Eble | B01F 7/1695 366/142 |
| 2015/0367303 A1 * | 12/2015 | Simon Soria | B01F 7/00725 |

FOREIGN PATENT DOCUMENTS

| | | |
|---|---|---|
| EP | 1874447 B1 | 11/2006 |
| EP | 1874448 A1 | 1/2008 |
| FR | 2929728 A1 | 10/2009 |
| WO | 2005124488 A1 | 12/2005 |

* cited by examiner

MIXING, STIRRING OR DISPERSING APPARATUS AND METHOD USING A CONTAINER WITH A DIAPHRAGM WALL PART WITH A DRIVE SWITCHED OFF CONDITION BASED ON A DIAPHRAGM LOADING CAPACITY

BACKGROUND

The invention relates to a mixing, stirring or dispersing method, in which a rod-shaped element which projects into a mixing chamber of a container and which is connected at the inlet into the mixing chamber to a diaphragm which is part of a wall of the container and, in order to process the contents of the mixing chamber, is made to move together with the diaphragm by a drive.

The invention also relates to a mixing, stirring or dispersing apparatus for carrying out the method mentioned at the beginning, having a container which has a mixing chamber, having a rod-shaped element which projects into this mixing chamber and has the purpose of transmitting force of a drive to the contents of the mixing chamber, and having a drive of this type which is located outside the mixing chamber, wherein the rod-shaped element is connected at the inlet into the mixing chamber to a diaphragm which is part of a wall of the container, and the rod-shaped element and the diaphragm can be made to move by the drive.

Such mixing, stirring or dispersing apparatuses are known, for example, from EP 1 874 447 B1 and EP 1 874 448 B1. In these apparatuses which are proven per se, the rod-shaped element which is connected to the diaphragm drives either a rotor arranged in the mixing chamber or milling elements which are to be introduced into the mixing chamber, with the result that these apparatuses serve to carry out the method.

However, while these apparatuses are operating it is possible for them to be damaged or destroyed during the execution of the method, and for the medium to be processed to escape, as a function of, at least, the rotational speed of the drive and therefore of the number of load changes of the diaphragm.

SUMMARY

There is therefore the object of providing a method of the specified type in which the medium can be prevented from escaping owing to damage to the diaphragm.

In order to meet this objective there is the provision that the number of revolutions of the drive is counted and when a maximum permissible number of revolutions for the loading capability of the diaphragm and the resulting number of load changes are reached the drive is switched off. As a result there is the possibility of ending a mixing, stirring or dispersing process in good time before failure, for example, in the form of tearing of the diaphragm. It is therefore possible to avoid a situation in which the medium to be processed undesirably escapes from the container.

In the case of toxic or contaminated media, the prompt aborting of the processing can prevent failure of the diaphragm and as a result reduce the health risk for a user which is caused when the media escape through the damaged diaphragm.

In this context it is possible for the user to switch off the drive, if appropriate manually, when the permissible number of load changes is reached. The potential wear part, here the diaphragm, can be deactivated and/or replaced preventively and in good time before a failure in a similar way as in the case of regular maintenance intervals such as are to be complied with, for example, when maintaining and repairing passenger cars.

It is particularly favorable if when the maximum permissible number of load changes for the diaphragm is reached the drive is switched off automatically. As a result, unsupervised execution of the method can also be possible since the drive can be switched off automatically and in good time before a damaging failure of the diaphragm.

It can be of particular significance for the method according to the invention if the maximum permissible number of load changes tolerated by the diaphragm is modified as a function of method parameters. The modification, that is to say adaptation, of the maximum permissible number of load changes tolerated by the diaphragm, as a function of method parameters may be appropriate because method parameters such as, for example, the rotational speed of the drive (revolutions per minute) the processing period of a method run, the temperature of the medium or chemical additives and/or components of the medium as well as further operating and method parameters which are not specified here can influence, and under certain circumstances reduce, the loading capability of the diaphragm and therefore its service life.

It is therefore conceivable for a relatively high rotational speed, which gives rise to a relatively high frequency of load changes of the diaphragm, to lead to earlier failure of the diaphragm compared to a relatively low rotational speed, even given an identical number of revolutions. In such a case it may be appropriate for the maximum permissible number of load changes tolerated by the diaphragm to be reduced as a function of this rotational speed.

For example, aggressive, acidic or alkaline media or other chemicals acting on the material of the diaphragm and/or of the container could also have a similar, service-life-shortening influence on the diaphragm, with the result that in these cases it may also be necessary to reduce the maximum permissible number of load changes.

In addition it may be expedient if the number of load changes and/or the number of revolutions of the drive is accumulated over a plurality of processing steps. This makes it possible for the loading experienced by the diaphragm which has already acted on the diaphragm during preceding processing steps to be combined and made available for comparison with the maximum permissible number of tolerated load changes.

Furthermore in this way a history of the container used for the method according to the invention and its diaphragm can be available, on the basis of which history the state and the capability of using the container and its diaphragm for future processing steps with the method can be estimated.

For this purpose it may be expedient if the accumulated number of load changes and/or the accumulated number of revolutions of the drive of a plurality of processing steps are stored. By storing the accumulated number of load changes of the diaphragm it is possible to record said number and, if appropriate, retrieve it again at a later time and/or employ it if required, for example, for a statistical evaluation.

It is particularly favorable here if the accumulated number of load changes of the diaphragm of a plurality of processing steps is assigned to the container which is respectively used for processing. The assignment of the accumulated number of load changes to the respective container may be appropriate particularly when the container is in the meantime removed from the drive and, for example, intermediately stored and/or combined with another drive. The assignment of this data can consequently facilitate the recording of a container-specific history of use.

The checking and/or monitoring of the diaphragm can also be facilitated if a warning in the form of a signal is issued before and/or when the permissible number of load changes predefined for the diaphragm is reached and/or exceeded. Through the prompt warning it is possible for a user to be alerted to the fact that the loading capability of the diaphragm has been reached and the drive is to be switched off, if appropriate manually, and/or the container replaced.

In particular in cases in which a user has to monitor a plurality of such mixing, stirring or dispersing apparatuses, the prompt displaying of a threat of failure of the diaphragm or of necessary replacement of the diaphragm and/or the container can avoid downtimes by informing the monitoring user. In this context it is also conceivable that even before the maximum number of load changes is reached a certain residual number of load changes and/or residual running time up to the time when the maximum number is reached is signaled or communicated.

In order to meet this objective, there is provision with the apparatus defined at the beginning that the apparatus has a counting unit for detecting the number of revolutions of the drive and the number of load changes of the diaphragm.

By using the counting unit, the number of load changes which loads the diaphragm during the execution of the method according to the invention can be determined. As a result, comparison of the counted load changes which have occurred with the maximum permissible number of load changes for the diaphragm is possible.

In this context it is favorable if the number of revolutions of the drive can also be accumulated over a plurality of processing steps using the counting unit in order to determine the number of load changes loading the diaphragm. By using the counting unit it is therefore also possible to record the number of revolutions of the drive and the resulting number of load changes of the diaphragm over a plurality of processing steps.

For this purpose it may be particularly expedient if a memory apparatus is provided for storing the number of revolutions of the drive accumulated over a plurality of processing steps in order to still be able to retrieve the number of revolutions of the drive which have taken place even at a later time. The memory apparatus can be embodied as a mechanical counting unit or else electronically, similarly to a kilometer counter or tachometer.

In order to signal to a user that a specific maximum number of load changes has been reached it may be expedient if the apparatus has a displaying apparatus and/or at least one signal generator.

It is particularly favorable if the signal generator is a sound generator and/or a lamp and/or some other signal source, for example a vibration alarm, which can be perceived by sensory means. As a result, the apparatus can alert a user to the fact that a predefined number of load changes has been reached.

In order to carry out the previously described method it may, in particular, be expedient if the drive has a switching apparatus in the form of control electronics which are connected to the counting unit in such a way that when the permissible number of revolutions is reached the drive can be switched off.

It may be particularly favorable here if when the permissible number of revolutions is reached the drive can be switched off automatically by the control electronics. This can permit unsupervised operation of the apparatus according to the invention and unsupervised execution of the method described at the beginning.

Furthermore it may be considered advantageous if the counting unit is an electronic, in particular software-implemented counting unit, and/or has evaluation electronics. Such a counting unit, which can be connected to the drive, simplifies internal communication of the elements provided in the apparatus with one another. Furthermore such a counting unit can already be integrated in the evaluation electronics or some other electronic component of the apparatus.

By using the evaluation electronics, the information made available by the counting unit and/or by further elements of the apparatus, such as, for example, the temperature, the pH value and/or the viscosity of a medium to be processed or of other media can be used by the apparatus to calculate the maximum permissible number of load changes for the diaphragm.

For this purpose it may be particularly favorable if the counting unit or the evaluation electronics or the control electronics contains a stored characteristic curve which represents the relationship between, on the one hand, the rotational speed and the number of revolutions of the drive and, on the other hand, the maximum permissible number of load changes representing the loading capability of the diaphragm. By means of the characteristic curve it is possible to take into account said load changes and also, if appropriate, previously specified operating parameters in the form of a mathematical model for the calculation and modification of the maximum permissible number of load changes.

It may be particularly favorable if the memory apparatus is arranged on the container. As a result, the number of load changes which have acted on the diaphragm as a result of processing steps with the respective container and as a result of the method can be assigned to this container and its diaphragm.

In particular when the container is removed or separated from the apparatus between two successive processing steps it may be appropriate to carry along the data relating to its processing history and loading capability with the container.

Assigning the operating data to a container is also conceivable within the apparatus itself. For this purpose, it is expedient if the container can be identified unambiguously in order to be able to assign the operating data to it. This identification can be carried out mechanically or electronically in a conventional way here.

It may be particularly appropriate if the maximum permissible value for the number of load changes for the diaphragm is stored in the memory apparatus. In particular if the maximum permissible value for the number of load changes is to be modified on the basis of varying operating parameters of operating processes which have already been carried out even during use of different containers, it may be necessary to assign to these containers different maximum permissible values for the numbers of load changes even for corresponding designs. It is favorable if this data is stored directly on the container.

An embodiment of the invention of particular significance may be that the memory apparatus is an RFID chip which can be read out and/or written on electronically, and the counting unit or the control electronics or the evaluation electronics has a transceiver unit for reading out and/or writing to the RFID chip in a wireless fashion. By using the transceiver unit it is then possible for the memory apparatus which is provided in the form of the RFID chip on the container to be read out and/or written to in a contactless fashion. In this context, connecting cables and/or other connecting means such as, for example, plug-type connections are avoided, with the result that the handling of the apparatus and/or the container is, for example, not adversely affected by cables or cable connections.

It may also be advantageous if the memory apparatus is arranged on and/or in the wall of the container. A memory apparatus which is positioned in such a way, in particular in the form of an RFID chip, may thus be particularly well protected against moisture, chemically aggressive media, shocks or other damaging environmental influences.

The operation and handling of the apparatus according to the invention can be facilitated by a displaying apparatus, in particular a display, for displaying in a particularly convenient way the information stored in the memory apparatus. It is therefore possible for a user to read out operationally relevant parameters from the memory apparatus and to cause them to be displayed by means of the display. This can simplify the control and execution of the method.

In addition it is possible that the memory apparatus can be programmed store and output additional information, in particular relating to the contents and/or the number of uses of the container. As a result, a virtually uninterrupted history, also relating to various operating parameters, of a container can be produced and retrieved again and, if appropriate, evaluated at any desired later time.

In order to be able to use a plurality of containers with the apparatus it is expedient if the container is detachably connected to the drive and/or to a housing containing the drive.

BRIEF DESCRIPTION OF THE DRAWINGS

Exemplary embodiments of the invention are described in more detail below with reference to the drawing in which, in, in some cases, highly schematic illustration.

DETAILED DESCRIPTION OF THE PREFERRED EMBODIMENTS

In the following description of various embodiments of the invention, elements which correspond in terms of their function are provided with corresponding reference numbers even when their configuration or shape differs.

Figure 1:
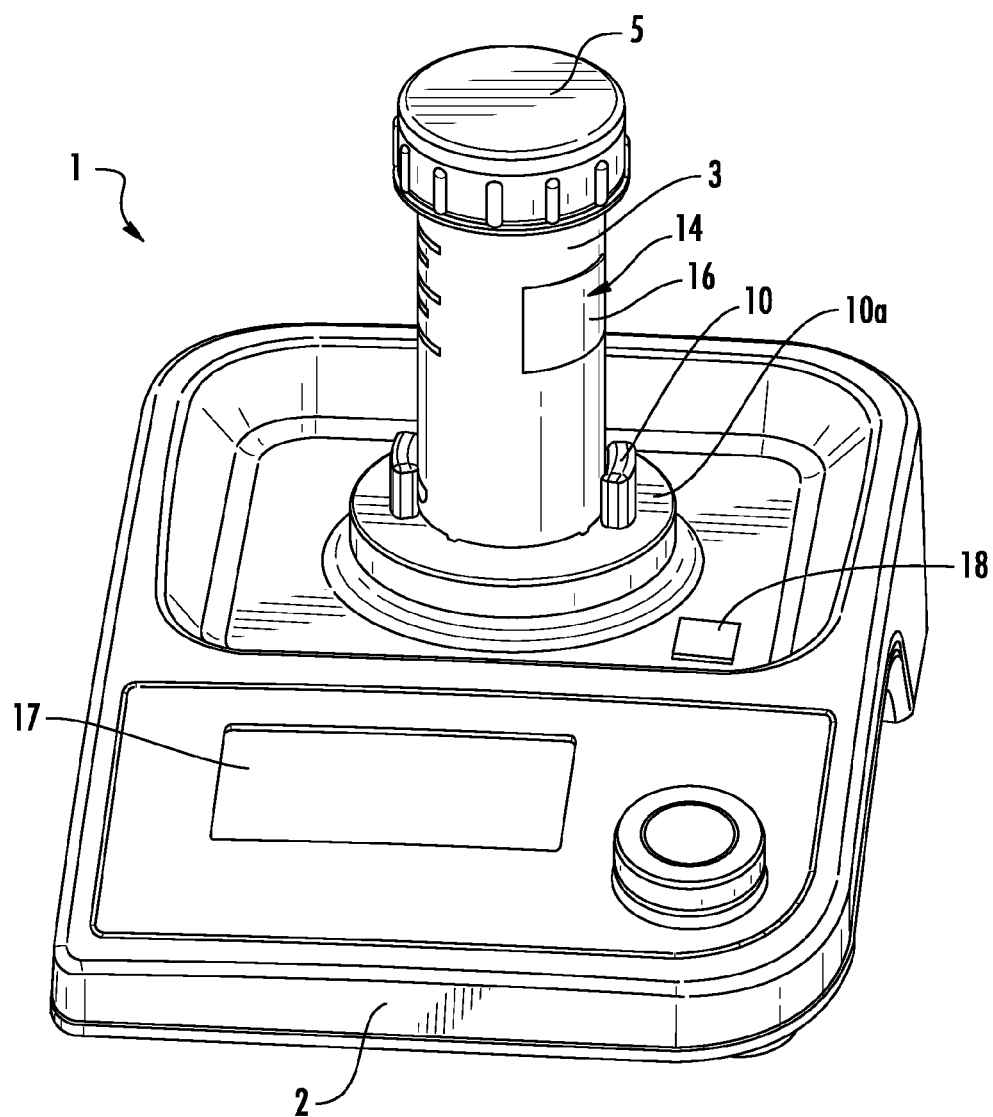
FIG. 1 shows a perspective external view of an apparatus according to the invention having a housing which has a display, a transceiver unit and a fitted-on container which contains a diaphragm and has a memory apparatus in the form of an RFID chip.

FIG. 1 shows a mixing, stirring or dispersing apparatus 1 having a substantially cylindrical, tube-shaped container 3 which is fitted onto the housing 2 thereof. According to FIGS. 2, 4 and 6, the container 3 has in its interior a mixing chamber 4 which is hermetically sealed in the exemplary embodiment by a screw lid 4.

A rod-shaped element 6 for transmitting force of a drive 7 onto the contents of the mixing chamber 4 of the container 3 projects into the mixing chamber 4. In this context, the rod-shaped element 6 is connected to a diaphragm 8 at the inlet into the mixing chamber 4 according to FIGS. 2, 4 and 6. This diaphragm 8 is part of a wall 9 of the container 3 and is made to move together with the rod-shaped element 6 via a coupling region 7a by the drive 7 of the apparatus 1.

The rod-shaped element 6 can interact here with a rotor or with milling elements, preferably balls, which are to be introduced into the mixing chamber, as is known, for example, from EP 1 874 447 B1 and EP 1 874 448 B1.

Figure 2:
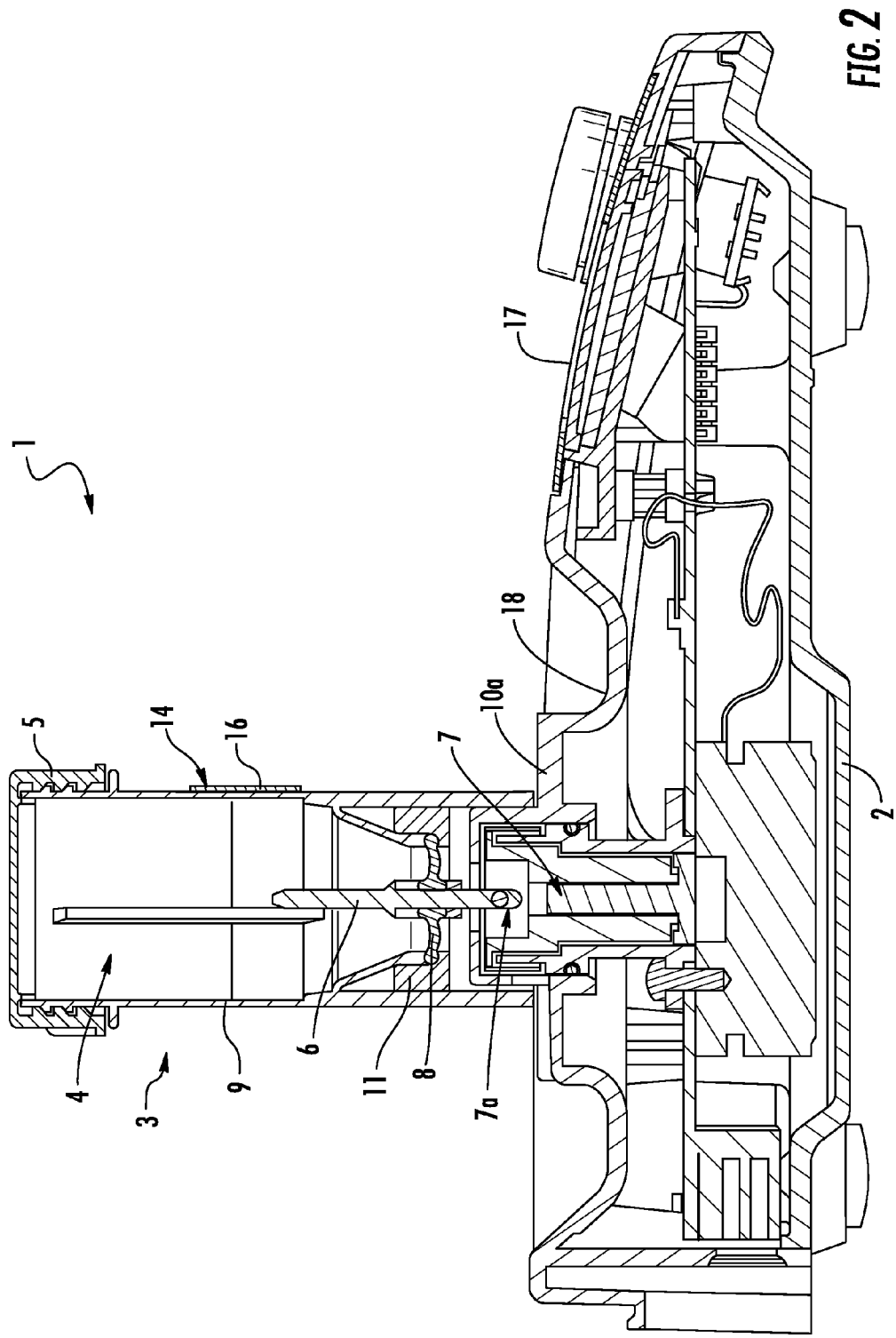
FIG. 2 shows a longitudinal section through the apparatus illustrated in FIG. 1, having a drive which is arranged in its interior and drives a rod-shaped element, connected to a diaphragm, for processing the medium in the mixing chamber of the container.

FIG. 2 shows that the drive 7 is arranged outside the mixing chamber 4 and underneath the container 3, fitted onto a receptacle socket 10a of the dispersing apparatus 1, within the housing 2 thereof. As is apparent in FIGS. 1 and 2, the container 3 can be detachably secured by means of securing aids in the form of bayonet closures 10 which interact with matching counterpieces on the receptacle socket 10a of the housing 2.

Figure 4:
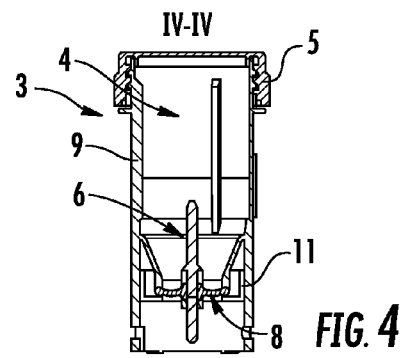
FIG. 4 shows a longitudinal section through the container along the line IV-IV in FIG. 3, wherein the diaphragm and the rod-shaped element which is connected to the diaphragm can be seen.
Figure 6:
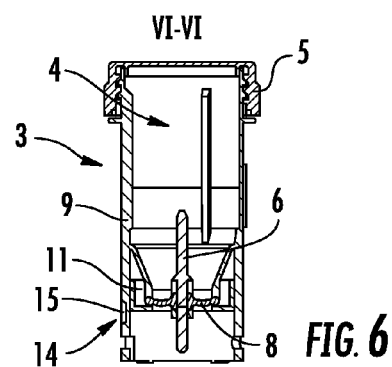
FIG. 6 shows a longitudinal section along the line VI-VI in FIG. 5, wherein an RFID chip is introduced into the wall of the container.

In FIGS. 2, 4 and 6 it is also apparent that the rod-shaped element 6 is connected to the diaphragm 8 in such a way that it penetrates it in a hermetically sealed fashion. The rod-shaped element 6 is secured together with the diaphragm 8 at the inlet into the mixing chamber 4 by means of an annular closure element 11, with the result that the diaphragm 8 forms part of the wall 9 of the mixing chamber 4. A materially joined connection between the diaphragm 8, the wall 9 and the rod-shaped element 6 would also be possible.

By means of the drive 7, the rod-shaped element 6 can be made to move in a wobbling fashion, as a result of which its end which is located in the mixing chamber 4 carries out a gyrating movement which also causes the diaphragm 8 connected to the rod-shaped element 6 to move in a tumbling fashion which deforms it to a certain extent, as a result of which the material of the diaphragm 8 can experience fatigue and failure.

The dispersing apparatus 1 is equipped with a counting unit in order to be able to detect the number of revolutions of the drive 7. This counting unit is implemented in the exemplary embodiment in the form of evaluation electronics 12 and illustrated schematically in FIG. 7.

The evaluation electronics 12 are in contact with the drive 7 via control electronics 13 and can therefore record the necessary information relating to the rotational speed and the number of revolutions of the drive 7.

Since the drive 7 interacts directly with the rod-shaped element 6 and the diaphragm 8, a revolution of the drive 7 results in a load change of the diaphragm 8, and said load change subjects the diaphragm 8 to wear as the number increases.

According to FIGS. 1, 2, 3 and 6, the dispersing apparatus 1 is equipped with a memory apparatus 14 which can be used to accumulate and store the number of revolutions of the drive 7, if appropriate also over a plurality of processing steps with the apparatus 1.

The memory apparatus 14 can be embodied here either in the form of an RFID chip 15 (cf. FIG. 6) or as what is referred to as an RFID tag 16 or as a RFID label which can be stuck on.

Figure 3:
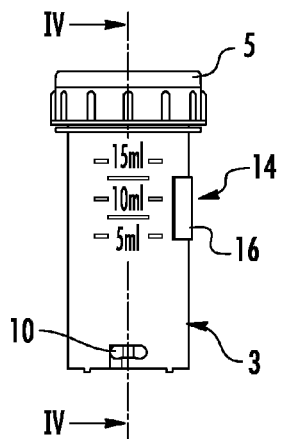
FIG. 3 shows a side view of the container which is illustrated in FIG. 1 and has an RFID chip which is attached to its wall.

FIG. 3 shows the use of an RFID tag 16 as a memory apparatus 14 on the outside of the container 3. This container 3 with the RFID tag 16 can also be seen in FIGS. 1 and 2.

Figure 5:
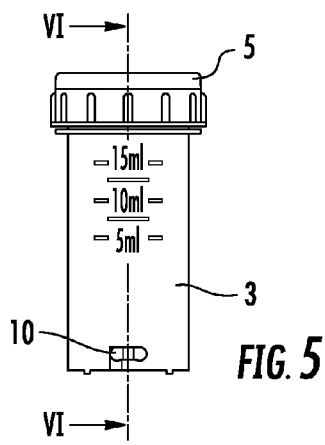
FIG. 5 shows an illustration of a modified container according to the invention corresponding to FIG. 3.

FIGS. 5 and 6 show an alternative embodiment of the container 3. In this context, the memory apparatus 14 in the form of an RFID chip 15 is let into the wall 9 near to the attachment point of the container 3, and is protected as a result.

According to FIG. 6, the RFID chip 15 is bonded in here within a depression in the wall 9 of the container. It is also possible to inject the RFID chip 15 into the wall 9 or mold it therein during the manufacture of the container.

The advantage of the RFID tag 16 according to FIGS. 1, 2 and 3 is that containers 3 can, if appropriate, also be subsequently equipped therewith.

In order to inform a user of the dispersing apparatus 1 that the diaphragm 8 has experienced a certain number of load changes, the dispersing apparatus 1 is equipped with a signal generator. In the exemplary embodiment, this signal generator is formed by a display 17 which is provided on the housing 2 of the dispersing apparatus 1.

The user can obtain various items of information relating to the ongoing processing and/or previously occurring processing from this display 17. Furthermore, a message for the user can appear on this display 17 as soon as the loading capability of the diaphragm 8 is reached by a certain predefined number of load changes. In embodiments which are not illustrated here it is also possible to provide further signal generators, for example in the form of sound generators, lamps or other signal sources, in particular vibration alarms, which can be perceived by sensory means, instead of or in addition to the display 17.

Figure 7:
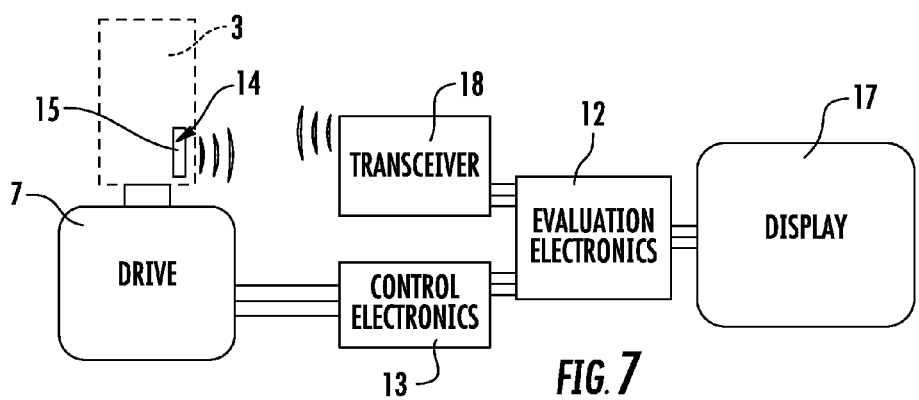
FIG. 7 shows a schematic illustration of the wiring of the elements of the apparatus which are involved in the execution of the method.

According to FIGS. 1, 2 and the schematic diagram in FIG. 7, the dispersing apparatus 1 is equipped with a transceiver unit 18 for reading out and/or writing on the RFID chip 15 or the RFID tag 16 in a wireless fashion. The transceiver unit 18 is connected here to the evaluation electronics 12 according to FIG. 7. The data received by the transceiver unit 18 from the memory apparatus 14 on the container 3 can therefore be processed directly by the evaluation electronics and passed on to the control electronics 13 which control the drive 7.

In particular when what is referred to as passive RFID technology, requiring energy fed in from the outside, is used, both the RFID chip 15 and the RFID tag 16 are fed with current via the transceiver unit 18 from an electromagnetic field which is emitted by this transceiver unit 18.

By using the bayonet closures 10, the container 3 is detachably connected to the drive 7 or to the housing 2 containing the drive 7. In this way it is possible to use different containers 3 with the same dispersing apparatus 1.

During use of the apparatus 1, the control electronics 13 supply the evaluation electronics 12 with the continuously updated number of revolutions of the processing operation which is being carried out at that time. This number is counted and recorded in the evaluation electronics 12. By using the container-specific information made available by the transceiver unit 18 from the memory apparatus 14 it is possible for the evaluation electronics 12 to modify, on the one hand as a function of the operating parameters, the maximum number of load changes which are to be defined as specific for the diaphragm 8 of the container 3 and, on the other hand, to update the total number of load changes carried out by the diaphragm 8.

The evaluation electronics 12 can shut down the drive by means of the control electronics 13 before failure of the diaphragm 8 occurs, by means of a comparison between the maximum permissible number of load changes and the number of load changes actually carried out up to this moment.

The drive 7 is switched off as soon as the maximum permissible number of revolutions is reached. This number is then transmitted via the transceiver unit to the memory apparatus 14 on the container 3 and stored there. If a container 3 has reached the maximum permissible number of load changes for its diaphragm 8, the evaluation electronics 12 can electronically lock out this container 3 of further use with the apparatus 1.

The apparatus 1 with a housing 2 and a container 3 is used in the mixing, stirring or dispersing method. The container 3 has in this context a mixing chamber 4 into which a rod-shaped element 6 projects. At the inlet into the mixing chamber 4, this rod-shaped element 6 is connected to a diaphragm 8 which is part of a wall 9 of the container 3. In order to process the contents of the mixing chamber 4, the rod-shaped element 6 is made to move together with the diaphragm 8 by a drive 7. In order to avoid unintentional failure of the diaphragm 8, the number of revolutions of the drive 7 is counted, and when a maximum permissible number of revolutions for the loading capability of the diaphragm 8 and the resulting number of load changes are reached the drive 7 is switched off.

What is claimed is:

1. A mixing, stirring or dispersing method, comprising: providing a rod-shaped element (6) which projects into a mixing chamber (4) of a container (3) and which is connected at an inlet into the mixing chamber (4) to a diaphragm (8) which is part of a wall (9) of the container (3) and, in order to process contents of the mixing chamber (4), moving the rod-shaped element together with the diaphragm (8) using a drive (7), counting a number of revolutions of the drive (7), and when a maximum permissible number of revolutions for a loading capability of the diaphragm (8) and a resulting number of load changes are reached, switching off the drive (7).

2. The mixing, stirring or dispersing method as claimed in claim 1, wherein when the maximum permissible number of load changes for the diaphragm (8) is reached the drive (7) is switched off automatically.

3. The mixing, stirring or dispersing method as claimed in claim 1, wherein the maximum permissible number of load changes tolerated by the diaphragm (8) is modifiable.

4. The mixing, stirring or dispersing method as claimed in claim 1, further comprising accumulating at least one of the number of load changes or the number of revolutions of the drive (7) over a plurality of processing steps.

5. The mixing, stirring or dispersing method as claimed in claim 4, wherein the accumulated number of load changes of the diaphragm (8) over the plurality of processing steps is assigned to the container (3) which is respectively used for processing.

6. The mixing, stirring or dispersing method as claimed in claim 1, further comprising storing at least one of an accumulated number of load changes or an accumulated number of revolutions of the drive (7) of a plurality of processing steps.

7. The mixing, stirring or dispersing method as claimed in claim 1, wherein a warning in the form of a signal is issued before or when the permissible number of load changes predefined for the diaphragm (8) is reached or exceeded.

8. The mixing, stirring or dispersing method as claimed in claim 1, wherein when a predefined number of load changes is reached or exceeded the drive (7) is switched off and the respective container (3) is electronically locked out of further use in the method.

9. A mixing, stirring or dispersing apparatus (1) comprising a container (3) which has a mixing chamber (4), having a rod-shaped element (6) which projects into the mixing chamber (4) that transmits a force of a drive (7) to contents of the mixing chamber (4), and having the drive (7) located outside the mixing chamber (4), the rod-shaped element (6) is connected at an inlet into the mixing chamber (4) to a diaphragm (8) which is part of a wall (9) of the container (3), and the rod-shaped element (6) and the diaphragm (6) are movable by the drive (7), and a counting unit for detecting a number of revolutions of the drive (7) and a number of load changes of the diaphragm (8).

10. The mixing, stirring or dispersing apparatus (1) as claimed in claim 9 wherein the number of revolutions of the drive (7) is accumulated by the counting unit over a plurality of processing steps in order to determine the number of load changes loading the diaphragm (8).

11. The mixing, stirring or dispersing apparatus (1) as claimed in claim 9, wherein a memory apparatus (14) is provided for storing data from the counting unit on the number of revolutions of the drive (7) accumulated over a plurality of processing steps.

12. The mixing, stirring or dispersing apparatus (1) as claimed in claim 11, wherein the memory apparatus (14) is arranged on the container (3).

13. The mixing, stirring or dispersing apparatus (1) as claimed in claim 11 wherein a maximum permissible value for the number of load changes for the diaphragm (8) is stored in the memory apparatus (14).

14. The mixing, stirring or dispersing apparatus (1) as claimed in claim 11, wherein the memory apparatus (14) is an RFID chip (15, 16) which can be at least one of read out or written to electronically, and the counting unit or control electronics (13) for the drive or evaluation electronics (12) of the counting unit has a transceiver unit (18) for reading out or writing to the RFID chip (15, 16) in a wireless fashion.

15. The mixing, stirring or dispersing apparatus (1) as claimed in claim 11 wherein the memory apparatus (14) is arranged at least one of on or in a wall (9) of the container (3).

16. The mixing, stirring or dispersing apparatus (1) as claimed in claim 11, wherein the apparatus (1) has a displaying apparatus for displaying information stored in the memory apparatus (14).

17. The mixing, stirring or dispersing apparatus (1) as claimed in claim 11, wherein the memory apparatus (14) is programmable to store and output additional information relating to contents or a number of uses of the container (3).

18. The mixing, stirring or dispersing apparatus (1) as claimed in claim 9, wherein the apparatus (1) has at least one of a displaying apparatus or at least one signal generator.

19. The mixing, stirring or dispersing apparatus (1) as claimed in claim 18, wherein the signal generator is at least one of a sound generator, a lamp, a vibration alarm, or another sensory output.

20. The mixing, stirring or dispersing apparatus (1) as claimed in claim 9, wherein the drive (7) has a switching apparatus in the form of control electronics (13) which are connected to the counting unit such that when a permissible number of revolutions is reached the drive (7) can be switched off.

21. The mixing, stirring or dispersing apparatus (1) as claimed in claim 9, wherein when the permissible number of revolutions is reached the drive (7) is switched off automatically by control electronics (13) for the drive.

22. The mixing, stirring or dispersing apparatus (1) as claimed in claim 9, wherein the counting unit is at least one of an electronic counting unit or has evaluation electronics (12).

23. The mixing, stirring or dispersing apparatus (1) as claimed in claim 22, wherein the counting unit or the evaluation electronics (12) or control electronics (13) for the drive contains a stored characteristic curve which represents a relationship between, a rotational speed and a number of revolutions of the drive (7) and the maximum permissible number of load changes representing a loading capability of the diaphragm (8).

24. The mixing, stirring or dispersing apparatus (1) as claimed in claim 9, wherein the container (3) is detachably connected to at least one of the drive (7) or to a housing (2) containing the drive (7).

* * * * *